United States Patent [19]

Zhu

[11] Patent Number: 5,891,181

[45] Date of Patent: Apr. 6, 1999

[54] BLOOD PRESSURE DEPRESSOR

[76] Inventor: Qiang Zhu, Zhongshan Garden, Room E.F, 9th Floor, No. 2 Building, Hangzhou, ZJ 310014, China

[21] Appl. No.: 929,258

[22] Filed: Sep. 15, 1997

[30] Foreign Application Priority Data

Dec. 23, 1995 [CN] China ............................. 96 2 50015.1

[51] Int. Cl.[6] ..................................................... A61N 1/18
[52] U.S. Cl. ................................................................ 607/44
[58] Field of Search .................................. 607/42, 44, 45, 607/2, 72, 75

[56] References Cited

U.S. PATENT DOCUMENTS

| 5,707,400 | 1/1998 | Terry ........................................... 607/44 |
| 5,727,558 | 3/1998 | Hakki et al. .............................. 607/44 |

Primary Examiner—Scott M. Getzow

Attorney, Agent, or Firm—Jinsu Z. Dai

[57] ABSTRACT

The present invention relates to a blood pressure depressor for depressing the hypertension in the human body. The device consists mainly of integrated circuits and several resisters, capacitors, light emitting diodes, ear electrodes, hand electrode, pocket and piezoelectric ceramic buzzer. Through a metal electrode contacted with a specific sensitive point of the human body a bioelectric current flows to a charge-discharge circuit which is connected with a electronic analogue switch circuit, an oscillating/frequency dividing circuit and an adjustable timing automatic alarm circuit to thereby attain the hypotensive and curative effect. It has a simple configuration and a convenient usage, and the blood pressure of a patient may be depressed by 10–40 mmHg through the use of it for 10 minutes. The cure rate reaches above 95% which shows a prominent curative effect, so that the device becomes a good doctor of the hypertension patients. It has no influence to the blood pressure of a normal person.

6 Claims, 4 Drawing Sheets

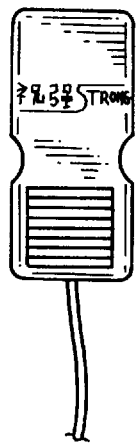
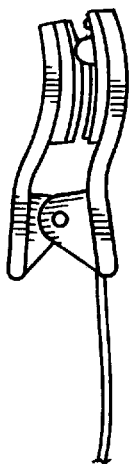
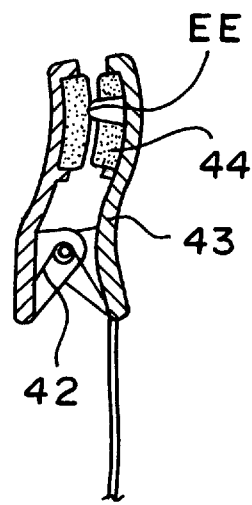
FIG. 6　　　FIG. 7　　　FIG. 8
FIG. 9　　　FIG. 10

BLOOD PRESSURE DEPRESSOR

FILED OF THE INVENTION

The present invention relates to a blood pressure depressor (hypotensive device) which can depress the hypertension as so called high blood pressure in the human body.

BACKGROUND OF THE INVENTION

Recently, there are a variety of devices and instruments for treating or depressing the hypertension on the market they have a certain curative effect upon the hypertension in the human body, but a number of unsatisfactory things still remain. For instance, a magnetic hat (a kind of hat incorporating a magnet which will be aligned with certain acupuncture point (acupoint) when it is in use), a hypotensive watch (a device with a magnet in it, having a watch-like form, which is worn on a hand and aligned with certain acupoint when in use), both have a unsatisfied curative effect. As a passive blood pressure depressor, for example, a curing device for depressing the hypertension is disclosed by a Chinese patent for utility model CN 2073758U. Referring to FIG. 1, there is shown a configuration of the curing device, when a curing electrode 4 is contacted with a certain sensitive position of the human body, and another curing electrode 5 is held with a hand, a bioelectricity (bioelectric current) will flow from the human body into an electrolytic capacitor 9 through a resistor 8 to charge the capacitor. During curing, a microswitch 2 should be operated intermittently with another hand over whole curing period, for discharging and recharging the capacitor 9. Accordingly, it is troublesome to operate this device, especially, the irregularity produced by manual operation makes a charge-discharge period unstable, as a result, the curative effect is unfavorably influenced. In addition, all the device above-mentioned have no timing function for automatic alarm, the curing period should be counted by a patient him-or herself. This may bring about another trouble to the patient, and the curing period and thus the preferred curative effect can not be optimally controlled.

SUMMARY OF THE INVENTION

To overcome above disadvantages, therefore, it is a primary object of the present invention to provide a blood pressure depressor of opening paragraph mentioned type which has a simple construction and a prominent curative effect, with optimal charge-discharge period can be simply operated, so that the trouble with the manual switching operation which is intermittent but lasts a long time span, can be eliminated.

It is another object of the present invention to provide a blood pressure depressor having both the optimal constant charge-discharge period and the automatic alarm function with adjustable timing.

According to a theory of channels and subsidiary channels of chinese traditional medicine and a principle of biophysics, combined with modern medicine, the investigation, diagnose and clinical practice have been conducted, and they has proved that the bioelectric potential in a hypotensive channel on ear back of a hypertension patient is obviously higher than that of a normal person, and on the contrary, the resistance in this channel of the patient is lower, so that the measure of the blood pressure in the human body can be directly influenced by controlling the level of the bioelectric potential.

Therefore, according to the present invention, there is provided a blood pressure depressor which has a charge-discharge circuit which is controlled by a time base circuit (timing axis oscillator) and a switch control circuit and connected with two ear electrodes and a hand electrode. Through the ear electrodes contacted each with the channel on an ear back of hypertension patient, the hand electrode held with the patient's hand and conductive wires the abnormal bioelectric potential at the channel on the ear back of the patient is conducted to the charge-discharge circuit. The charge-discharge circuit has a constant charge-discharge period, so that the bioelectricity is dissipated in the charge-discharge circuit through a number of repetitional charging and discharging operation, that is, this makes the bioelectric current discharged in a manner of fixed time and fixed quantity, thus, the abnormal bioelectric potential is reduced, the bioelectricity and resistance in the human body are tending towards normality. Therefore, the object of depressing the hypertension is properly reached.

According to another embodiment of the present intention, the blood pressure depressor has a time base circuit, a switch control circuit, a charge-discharge circuit which is controlled by the time base circuit, the switch control circuit and connected with two ear electrodes and a hand electrodes, an operation indicating circuit, and a music alarm circuit controlled by an adjustable time base circuit and a triggering circuit. Through the ear electrodes contacted each with the channel on an ear lack of a hypertension patient, the hand electrode held with the patient's hand and conductive wires the abnormal bioelectric potential at the channel on the ear back of the patient is conducted to the charge-discharge circuit. The charge-discharge circuit has a constant charge-discharge period, so that the bioelectricity is dissipated in the charge-discharge circuit through a number of repetitional charging and discharging operation, that is, this makes the bioelectric current discharged in a manner of fixed time and fixed quantity. Thus, the abnormal bioelectric potential is reduced, the bioelectricity and resistance in the human body are tending towards normality, therefore the, object of depressing the hypertension is properly reached. During curing, the charge-discharge state is indicated by the operation indicating means and the curing period is controlled by the adjustable time bade circuit. The alarm signal will be sent out as a music sound from the music alarm circuit when the cure comes to the end.

BRIEF DESCRIPTION OF THE DRAWINGS

FIG. 6 is a schematic view of an ear electrode;

FIG. 7 is a side view of FIG. 6;

FIG. 8 is a sectional view of FIG. 7;

FIG. 9 is a schematic view of a hand electrode; and

FIG. 10 is a side view of FIG. 9;

DETAIL OF THE INVENTION

Figure 1:
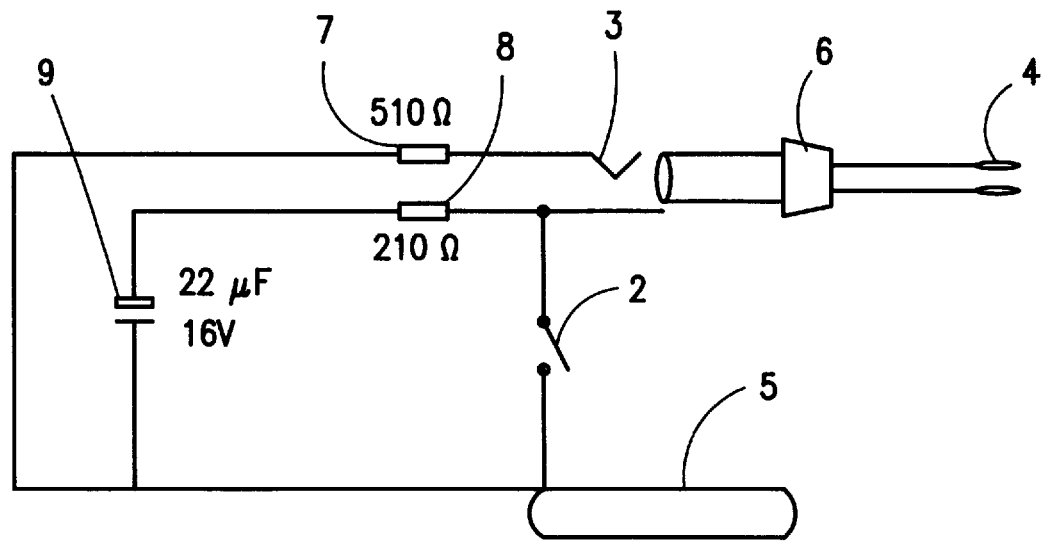
FIG. 1 is a principle scheme showing a blood pressure depressor according to a prior art.
Figure 11:
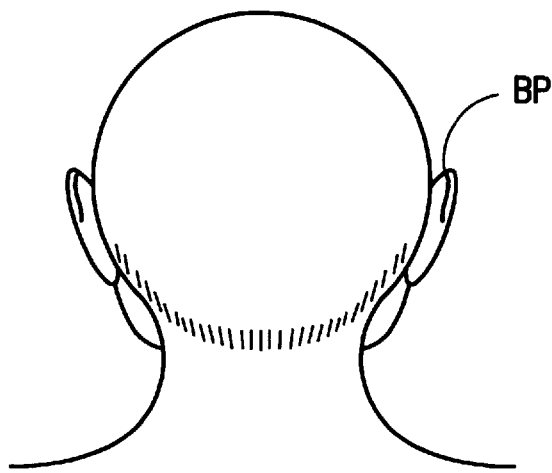
FIG. 11 shows a rear view of a human head.

In the following the operational principle of a blood pressure depressor (hypotensive device) according to the present invention will be described. Referring to the block diagram of FIG. 2, a time base circuit generates a signal of control pulse which controls a switch control circuit. The switch control circuit in turn is going to control a charge-discharge circuit which will perform the charge-discharge operation.

The arrangement of the blood pressure depressor according to the invention will be described with referring to the circuit diagram shown in FIG. 3. In this figure, the pins 9,10,and 11 of a first integrated circuit $C_1$ are connected with the first terminals of a capacitor $C_1$ and resistors $R_1$ and $R_2$, respectively, while the second terminals of the capacitor $C_1$ and resistors $R_1$ and $R_2$ are connected together with each other. One terminal of a resistor $R_3$ is connected with the positive pole of a DC power supply, and the other terminal is connected with the pin 12 of the first integrated circuit $IC_1$ and the anodes of two diodes $D_1$ and $D_2$. The cathodes of the both diodes $D_1$ and $D_2$ are connected with pins 15 and 3 of the first integrated circuit $IC_1$. A control pulse signal PST is output from pin 3 of the first integrated circuit $IC_1$ and input directly to pins 5,6 and 11 of the second integrated circuit IC2.

The time base circuit consists of the resistors $R_1$, $R_2$ and $R_3$, the capacitor $C_1$, diodes $D_1$ and $D_2$, and the first integrated circuit $IC_1$, wherein the resistors $R_1$ and $R_2$, the capacitor $C_1$ and the pins 11, 10 and 9 of the first integrated circuit $IC_1$ constitute a RC oscillator, whose oscillating frequency depends on a product $R_2\ C_1$. The product $R_2\ C_1$ is a time constant which can be adjusted by adjusting the resistance of $R_2$ or changing the capacitance of $C_1$. The resistor $R_3$, diodes $D_1$ and $D_2$ and the pins 3, 12 and 15 of the first integrated circuit $IC_1$ constitute a frequency dividing circuit. The time constant $R_2\ C_1$ is so adjusted that a low level with a duration of 15~60 second and a high level with a duration of 1~4 second can be output from the pin 3 of the first integrated circuit $IC_1$. In order to achieve an optimal curative effect, in this device a fixed capacitor $C_1$ and an adjustable resister $R_2$ are adopted, and the periodical wave form of the output signal PST from the Pin 3 of the first integrated circuit $IC_1$ has a low level with a duration of 30±2 seconds and a high level with a duration of 2±0.2 seconds.

The pins 2 and 14 of the second integrated circuit $IC_2$ are connected with the positive pole Vcc of the DC power supply, and the pins 4,7,9 and 11 of second integrated circuit $IC_2$ are grounded. A green light emitting diode $LED_1$ having its anode connected with the positive pole Vcc of the DE power supply and its cathode connected with the pins 3 and 13 of the second integrated circuit $IC_2$ is connected to a resistor $R_4$ in parallel. The pin 8 of the second integrated circuit $IC_2$ is connected with a plus terminal of a capacitor $C_3$ and one terminal of a socket CZ, and pin 10 of second integrated circuit $IC_2$ is connected to a plus terminal of a capacitor $C_2$ and the other terminal of the socket CZ. And a red light emitting diode $LED_2$ has its anode connected with the pin 1 of the second integrated circuit $IC_2$ and its cathode grounded. A hand electrode M is directly grounded.

The integrated circuit $IC_2$ and its peripheral elements connecting with it constitute a switch control circuit. The control pulse signal PST from the pin 3 of the first integrated circuit $IC_1$ is immediately sent to the pins 5, 6, and 12 of the second integrated circuit $IC_2$, to control directly the three analogue switches, i.e. the pins 3 and 4, 8 and 9, and 10 and 11 of the integrated circuit $IC_2$, wherein for the two switches or branches ( the pins 8 and 9 and the pins 10 and 11) the pins 9, 11 of them are grounded and the other pins 8 and 10 of them are connected with the socket's terminals, respectively. And the capacitors for storing energy $C_3$ and $C_2$ connected respectively in parallel with the two analogue switches, i.e. the both ends of two pair pins 8 and 9, 10 and 11, constitute a charge-discharge circuit.

When the signal PST from the pin 3 of the,integrated circuit $IC_1$ is at its low level with the duration of 30 seconds, the analogue switches of pins 8 and 9, 10 and 11 of the second integrated circuit $IC_2$ are disconnected, and the bioelectric current from the human body flows to the capacitors $C_2$ and $C_3$ through the ear electrode EE and the socket CZ to charge the capacitors $C_2$ and $C_3$. When the signal PST from the pin 3 of the first integrated circuit $IC_1$ becomes its high level with the duration of 2 seconds, the analogue switches of pins 8 and 9, 10 and 11 are switched on, to discharge the bioelectricity charged on the energy storing capacitors $C_2$ and $C_3$.

As mentioned above, when the signal PST from the pin 3 of the integrated circuit $IC_1$ is at the low level with the duration of 30 second, the analogue switches of pin 3 and 4, 8 and 9, 10 and 11 of the second integrated circuit $IC_2$ are all disconnected, and the capacitors $C_2$ and $C_3$ are charged, so that the green light emitting diode $LED_1$ connected in series with a analogue switch and DC power supply is turned off and is nonluminous. Since the resistor $R_4$ is connected in parallel with the green light emitting diode $LED_1$, this brings the potential of pin 13 of the integrated circuit $IC_2$ on a high level. And since this potential of pin 13 of the second integrated circuit $IC_2$ controls the analogue switch of pins 1 and 2, as a result, the pins 1 and 2 are connected with each other a current flows through the red light emitting diode $LED_2$ and makes it luminous. That is, the charge state of the capacitors $C_2$ and $C_3$ is indicated by the red light emitting diode $LED_2$.

When the signal PST from the pin 3 of the integrated circuit $IC_1$ is at its high level with the duration of 2 second, the analogue switches of pins 3 and 4, pins 8 and 9 and pins 10 and 11 are all closed, and the capacitors $C_2$ and $C_3$ are discharged, so that the green light emitting diode $LED_1$ gets a current and is luminous. And the closure of pins 3 and 4 brings the potential of pin 13 of the integrated circuit $IC_2$ on a low level, as a result, the pin 1 and 2 are disconnected with each other, no current flows through the red light emitting diode $LED_2$ and makes it nonluminous. That is, the discharge state of the capacitors $C_2$ and $C_3$ is indicated by the green light emitting diode $LED_1$.

Figure 4:
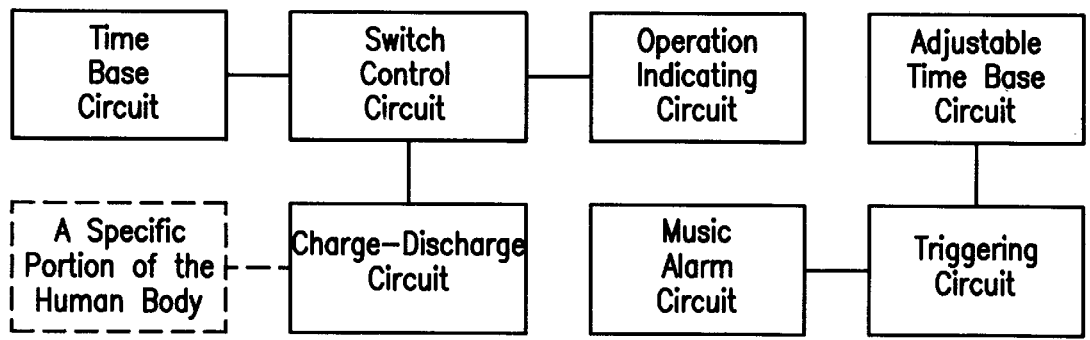
FIG. 4 is a schematic block diagram of a blood pressure depressor according to another embodiment of the present invention.

Next, the operational principle of a blood pressure depressor according to the other embodiment of the invention will be further described in conjunction with the block diagram shown in FIG. 4. Similar to above, a time base circuit generates a control pulse signal which controls a switch control circuit. In addition, an adjustable timing circuit, a triggering circuit and an automatic alarm circuit for warning the patient are provided, Referring to FIG. 5, there is shown a concrete arrangement of this circuitry, the pins 9, 10, and 11 of the third integrated circuit $IC_3$ are connected with the first terminals of a capacitor $C_4$ and resistors $R_7$ and $R_5$, respectively. The second terminal of the resistor $R_7$ is connected with the first terminals of a resistor $R_6$ and a potentiometer W, while the second terminals of the capacitor $C_4$, the potentiometer W, the resistors $R_5$ and $R_6$ are all connected to a node C, The pin 12 of the integrated circuit $IC_3$ is connected with the minus terminal of a capacitor $C_5$ and one terminal of a resistor $R_8$, and the plus terminal of the capacitor $C_5$ and the other terminal of the resistor $R_8$ are connected with the positive pole Vcc of D.C. power supply and earth, respectively, The pin 3 of the third integrated circuit $IC_3$ is connected to the pin 1 of the fourth integrated circuit $IC_4$ through a resistor $R_9$. The pins 3 and 4 of the fourth integrated circuit CI4 are connected with a ceramic buzzer HTD which is connected with a capacitor $C_6$ in parallel.

Figure 2:
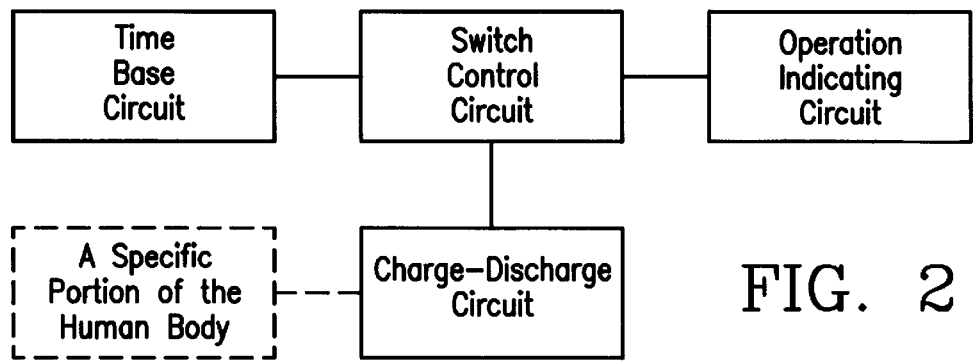
FIG. 2 is a schematic block diagram of a blood pressure depressor according to an embodiment of the present invention.
Figure 3:
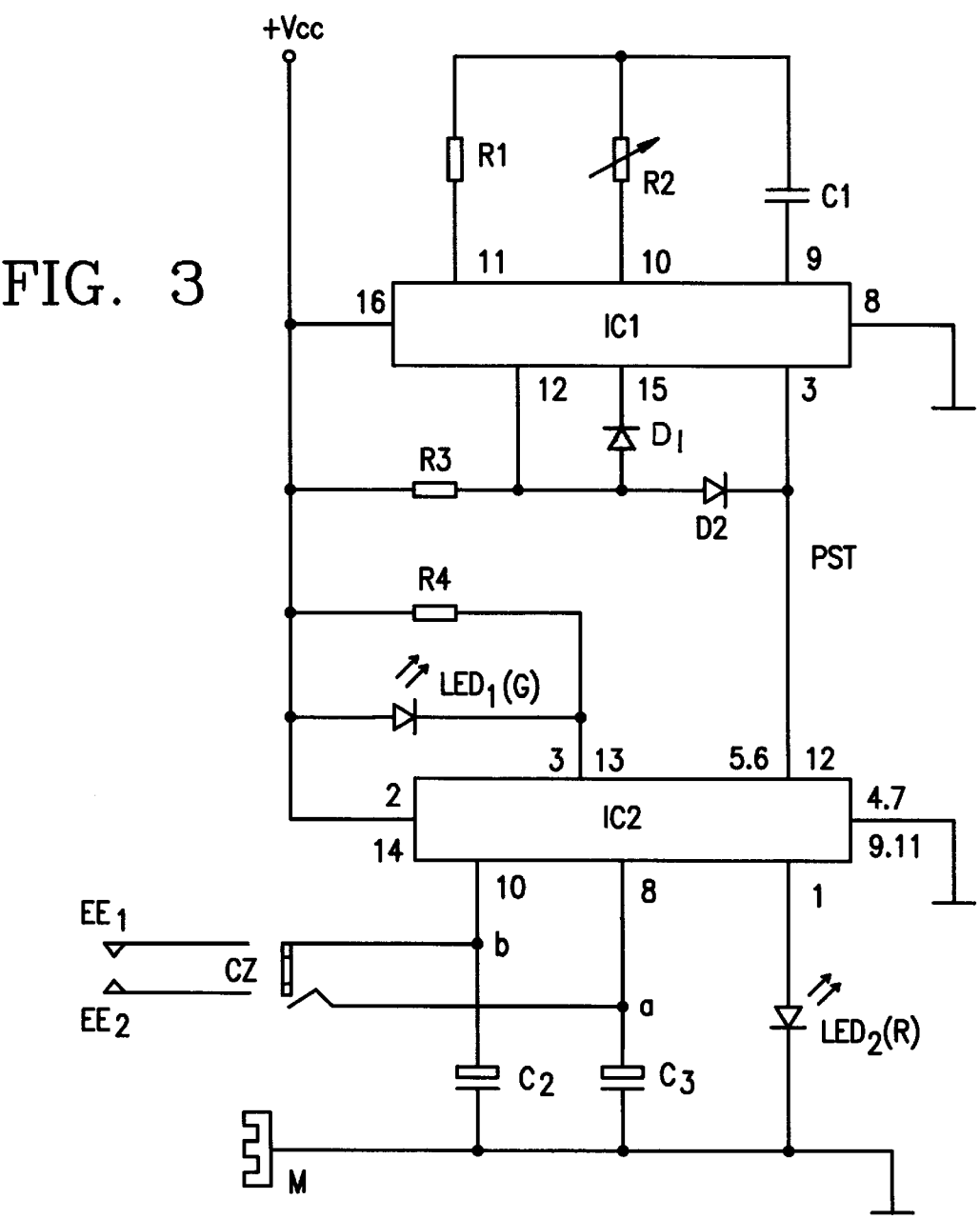
FIG. 3 is a concrete circuit diagram of a blood pressure depressor according to the embodiment of the present invention.
Figure 5:
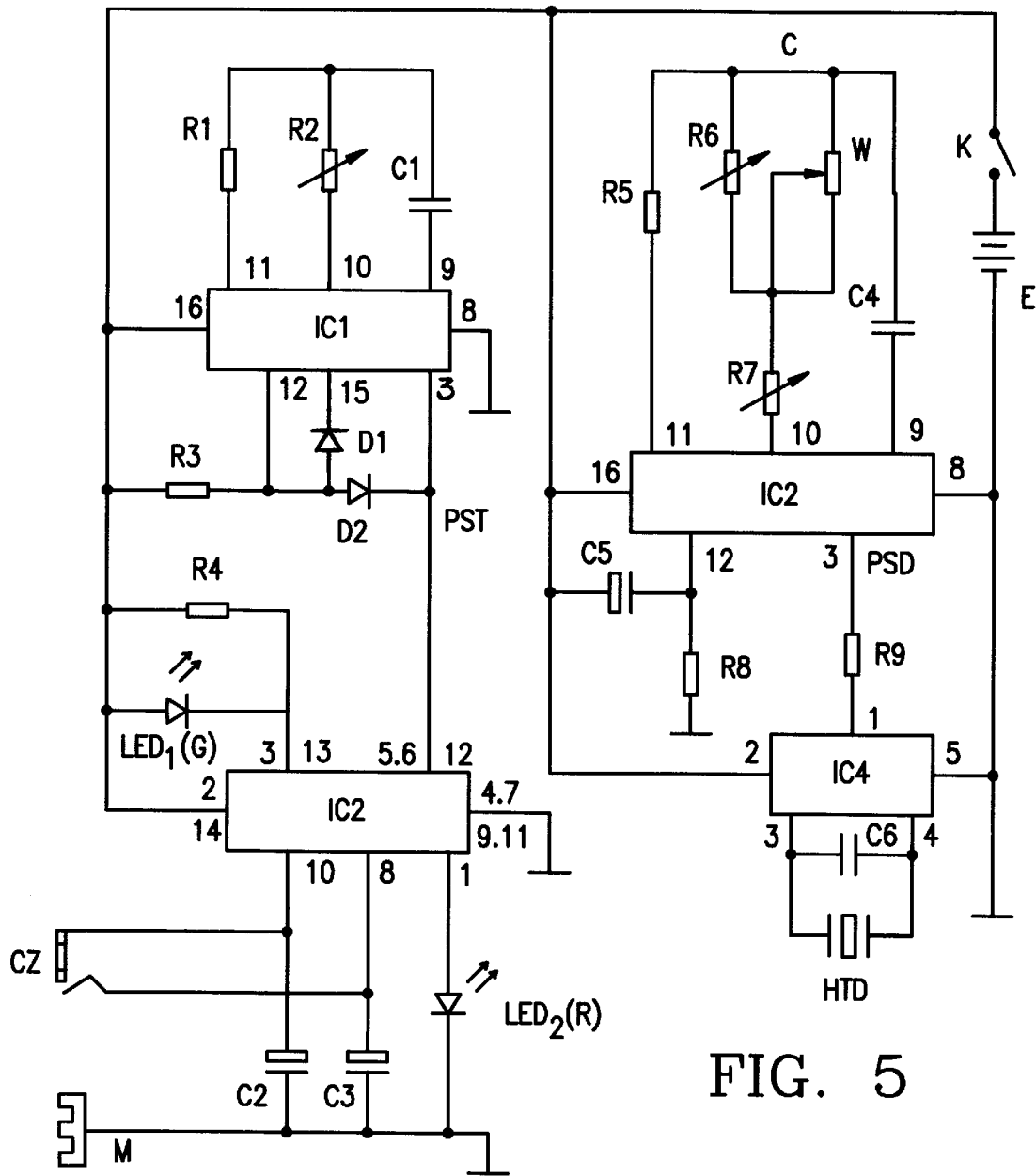
FIG. 5 is a concrete circuit diagram of a blood pressure depressor according to the another embodiment of the present invention.

The time base circuit, the control circuit and the charge-discharge circuit in FIG. 4 and 5 are all the same as that in FIG. 2 and 3, so the description for them is omitted. In addition, the resistors $R_5$, $R_6$, $R_7$ and $R_8$, the potentiometer W, the capacitors $C_4$ and $C_5$, and the third integrated circuit $IC_3$ constitute an adjustable time base circuit. When a switch K is opened, there is no voltage across the capacitor $C_5$, and potential on the pin 12 of the third integrated circuit $IC_3$ becomes a high level, so that the third integrated circuit $IC_3$ is reset. Upon the charging of capacitor $C_5$ through the resistor $R_8$, the potential on the pin 12 of the third integrated circuit $IC_3$ is gradually reduced and will become a low level after about 2~3 seconds when the switch K is closed Then the third integrated circuit CI3 begins to work. The resistors $R_5$, $R_6$ and $R_7$, the potentiometer W, capacitor $C_4$ and the pins 11, 10 and 9 of the third integrated circuit $IC_3$ constitute an adjustable RC oscillator of which the highest oscillating frequent is set by adjusting the resistor $R_7$, the lowest oscillating frequency is set by adjusting the resistor $R_6$, and a middle frequency between the highest and lowest frequencies can be arbitrarily set by adjusting the value of the potentiometer W. The oscillating frequency of the third integrated circuit $IC_3$ is divided through inner multistage frequency dividers into a signal PSD which output from the pin 3 of the integrated circuit $IC_3$. When the oscillating frequency is at the highest/the lowest, the duration for which the pin 3 of $IC_3$ is at a low level is 10/15 minutes, respectively. The potential of pin 3 of the third integrated circuit $IC_3$ will be transited to a high level after 10~15 minutes of low level time. The signal PSD having high level from the pin 3 of the integrated circuit $IC_3$ is applied to the pin 4 of the fourth integrated circuit $IC_4$ through a resistor $R_9$ to trigger the music module of the integrated circuit $IC_4$ into operation. When the integrated circuit $IC_4$ is triggered, an audio signal from its pins 3 and 4 is applied to the piezoelectric ceramic buzzer HTD to bring the latter into a "music performance" The capacitor $C_6$ is arranged to filter off high-frequency component from the audio signal. The music sound sent out by the piezoelectric ceramic buzzer HTD is going to warn a patient that a predetermined time is over. Once the curing comes to the end, the device may be turned off.

The pins 16 of the integrated circuits $IC_1$ and $IC_3$, the pin 14 of the integrated circuit $IC_2$ and the pin 2 of the integrated circuit $IC_4$ are all connected to the positive pole of D.C. power supply E through the switch K which is arranged to govern the power supply to this blood pressure depressor. The pins 8 of the integrated circuits $IC_1$ and $IC_3$, the pin 4 and 7 of the integrated circuit $IC_2$ and the pin 5 of the integrated circuit $IC_4$ are all grounded. In this circuitry are adopted:

IC module type 4046 (a multistage counter/divider with oscillator) as the integrated circuits $IC_1$ and $IC_3$ IC module type 4066 (a electronic analogue switches) as the integrated circuit $IC_2$;

a music module as the integrated circuit $IC_4$; and the rocket CZ is a socket for ear electrode.

Now the ear electrode will be described with reference to FIG. 6. The ear electrode EE made of a metal, preferably, the copper is fixed in an ear clip which is constructed with a spring 42 and two plastic plates 43 on which each sponge pad 44 is bonded. The ear electrode is embedded into a sponge pad 44.

Then, the hand electrode will be described with reference to FIG. 7. The hand electrode made of a metal, preferably, zinc, is a integral electrode with three convex blocks, which has a "E" configuration.

When this blood pressure depressor is in use, two ear clips are clipped on the two ears of a patient with each ear electrode aligned with a hypotensive channel BP on each ear back (referring to FIG. 6 and 8). A bioelectric current from the human body will flow into the blood pressure depressor through the ear electrodes in the ear clips, conductive wires and the rocket. The right hand of the patient holds (presses) blood pressure depressor, the middle, the ring and the little fingers contact respectively the three convex blocks of the hand electrode M. Then the switch of the device is turned on, for example, by the let hand, the blood pressure depressor begins to work and the light emitting diodes will indicate its operational states. The present depressor has a constant charge-discharge period i.e. 15~60 second for charging and 1~4 second for discharging which are indicated by the red and green light emitting diodes, respectively.

It is proved that a prominent curative effect is achieved on the hypertension patients when the analogue switches, i.e. the pins 8 and 9, 10 and 11 of IC2 are opened (to charge capacitors ) for 15~60 second and closed (to discharge) for 1~4 second, wherein the opened (charging) time of 30 second and the closed (discharging) time of 2 second of the analogue switches brings out the optimal curative effect. A detailed hypotensive effect may refer to the report of clinical practice of the following table.

TABLE

The Influence of Charge-Discharge Period on the Curative Effect (kPa)

| Charge-dis | Charging for 15 s discharging for 1 s | | charging for 22.5 s discharging for 1.5 s | | Charging for 30 s discharging for 2 s | | Charging for 45 s discharging for 3 s | | Charging for 60 s discharging for 4 s | |
|---|---|---|---|---|---|---|---|---|---|---|
| charge period date | before curing | after curing | before curing | after curing | before curing | after curing | before curing | after curing | before curing | after curing |
| 1st day | 21.5/13.3 | 19.8/11.9 | 21.7/13.4 | 20.3/12.4 | 21.4/13.2 | 19.8/11.9 | 21.3/13.2 | 19.6/11.8 | 21.4/13.0 | 19.7/11.7 |
| 2nd day | 21.3/13.2 | 20.3/12.1 | 21.5/13.2 | 19.8/12.1 | 21.1/12.0 | 18.8/11.9 | 19.8/12.0 | 19.1/11.3 | 21.3/12.4 | 20.0/12.1 |
| 3rd day | 20.5/12.3 | 19.4/11.7 | 21.1/12.2 | 19.7/11.9 | 20.5/12.1 | 18.5/11.6 | 20.3/12.1 | 18.8/11.8 | 20.8/11.8 | 20.1/11.7 |
| 4th day | 20.7/12.2 | 19.9/11.8 | 20.9/12.0 | 19.2/11.3 | 20.4/12.1 | 19.0/11.1 | 20.0/12.1 | 18.6/11.3 | 20.6/11.7 | 19.7/11.5 |
| 5th day | 20.6/12.1 | 19.7/11.8 | 20.7/12.0 | 19.3/11.5 | 19.4/12.1 | 18.7/11.1 | 20.0/11.8 | 18.8/11.2 | 20.5/11.7 | 19.5/11.5 |
| 6th day | 20.4/12.0 | 19.5/11.6 | 20.5/11.9 | 19.2/11.3 | 19.8/11.6 | 18.6/10.8 | 19.8/11.7 | 18.7/11.0 | 20.3/11.6 | 19.4/11.4 |
| 7th day | 20.3/12.0 | 19.4/11.6 | 20.4/11.9 | 19.1/11.2 | 19.6/11.7 | 18.7/10.8 | 19.7/11.7 | 18.7/11.0 | 20.2/11.6 | 19.4/11.4 |

TABLE-continued

The Influence of Charge-Discharge Period on the Curative Effect (kPa)

| Charge-dis charge period date | Charging for 15 s discharging for 1 s | | Charging for 22.5 s discharging for 1.5 s | | Charging for 30 s discharging for 2 s | | Charging for 45 s discharging for 3 s | | Charging for 60 s discharging for 4 s | |
|---|---|---|---|---|---|---|---|---|---|---|
| | before curing | after curing | before curing | after curing | before curing | after curing | before curing | after curing | before curing | after curing |
| Hypotensive range | 2.1/1.7 | | 2.6/2.2 | | 2.7/2.4 | | 2.6/2.2 | | 2.0/1.6 | |

Note  each curing period is 10 minutes

Therefore, the optimal scheme is that the preferable opened (charging) time and closed (discharging) time are 30 second and 2 second, respectively, which will be adopted in a current prototype of the blood pressure depressor.

The music performing moment may be changed by adjusting a knob of the potentiometer W, so the curing time can be set arbitrarily in a range of 10~15 minutes. When the curing time is over, the blood pressure depressor gives out a clear, melodious, gentle and sweet music voice to warn the patient that, the device may be shut off. A great number of clinical practicing cases have proven that blood pressure of a patient may be depressed by 13.4~30 kPa after each curing for 10 minutes. The factor of the curative effect reaches to 96%, moreover it has no any influence to the blood pressure of a normal person.

To sum up, the present blood pressure depressor has a simple configuration convenient usage and prominent curative effect and will become a good 'doctor' of the hypertension patients.

While the present invention has been described through the particulars embodiments and the accompanying drawings, the present invention should not be limited to the particular embodiments and the accompanying drawings, it will be apparent to those skilled in the art that various changes, modifications and replacements in form and in detail may be made, without departing from the spirit and scope of the invention as defined in the following claims.

What is claimed is:

1. A blood pressure depressor for depressing the hypertension in the human body having a time base circuit, a switch control circuit and a charge-discharge circuit, wherein said time base circuit comprising: a first integrated circuit ($IC_1$), a capacitor ($C_1$) having the first terminal connected with the pin 9 of said integrated circuit ($IC_1$) and the second terminal connected with the second terminals of a variable resistor ($R_2$) and a resistor ($R_1$) whose first terminals are connected with the pins 10 and 11, respectively; a resistor ($R_3$) being connected between the pins 12 and 16; a first diode ($D_1$) having a anode connected to the pin 12 and a cathode connected to the pin 15; a second diode ($D_2$) having a anode connected to the pin 12 and a cathode connected to the pin 3 from which is output a control pulse signal (PST) having a pulse duration of 1~3 second and a period of 1 second~60 second for controlling a timing circuit; and a DC power supply having positive pole connected with the pin 16 and negative pole grounded;

said switch control circuit comprising : a second integrated circuit ($IC_2$) of which the pins 5, 6 and 12 receive the control pulse signal (PST) to control a connecting or a disconnecting state of the pins 1 and 2, pins 3 and 4, pins 8 and 9, and pins 10 and 11; and said charge-discharge circuit comprising: two charge capacitors ($C_2$ and $C_3$) having a plus terminals connected with the pins 8 and 10 of the second integrated circuit ($IC_2$), and having a minus terminals grounded; two ear electrodes ($EE_1$ and $EE_2$) being connected through a socket (CZ) to the pins 8 and 10 of the second integrated circuit $IC_2$ whose pins 9 and 11 are grounded; a hand electrode (M) being directly grounded; when the pins 8 and 9, pins 10 and 11 are at their disconnecting state, the two ear electrodes ($EE_1$ and $EE_2$), the ears and the hand of the human body and the hand electrode (M) constitute a charge circuit of the capacitors ($C_2$ and $C_3$).

2. A blood pressure depressor for depressing the hypertension in the human body according to claim 1, further comprising:

a operation state indicating means for indicating the operation state of said depressor, said operation state indicating means having a green light emitting diode ($LED_2$) connected between the positive terminal of D. C. power supply (Vcc) and the pins 3 and 13 of the second integrated circuit ($IC_2$), for indicating the discharging state and a red light emitting diode ($LED_1$) connected between the pin 1 of the second integrated circuit ($IC_2$) and earth, for indicating the charging state.

3. A blood pressure depressor for depressing the hypertension in the human body according to claim 2, further comprising:

an adjustable timing circuit, a triggering circuit and a music alarm circuit, wherein said adjustable timing circuit comprising: a third integrated circuit ($IC_3$) of which the pins 11, 10 and 9 are connected respectively with the first terminals of a resistor ($R_5$), a variable resistors ($R_7$) and a capacitor ($C_4$) ;a variable resistor ($R_6$) and a potentiometer W both having first terminals connected with the second terminal of said resistor ($R_7$) and a second terminals connected with the seconds terminal of said resistor ($R_5$) and said capacitor ($C_4$); a capacitor $C_5$ being connected between the pin 16 and pin 12; a resistor $R_8$ being connected between the pin 12 and earth ; a switch K being connected between the pin 16 and the positive terminal Vcc of D. C. power supply whose negative terminal is connected to the pin 8 and earth; when the switch K is closed, a control pulse signal (PSD) having a pulse duration of 1~3 second and a period of 10–15 minutes is output from the pin 3, said triggering circuit comprising: a fourth integrated circuit $IC_4$ of which a input pin 1 receives the control pulse signal (PSD) output from the third integrated circuit ($IC_3$) through resistor ($R_9$), and a capacitor ($C_6$) being connected between the pins 3 and 4 of the fourth integrated circuit ($IC_4$), and said music alarm circuit comprising: a ceramic buzzer (HTD) having two terminals connected with the capacitor $C_6$ in parallel between the pins 3 and 4 of the fourth integrated circuit ($IC_4$).

4. A blood pressure depressor for depressing the hypertension in the human body according to claim 2, wherein said hand electrode (M) being a integral electrode with three convex blocks made of zinc and having a 'E' configuration.

5. A blood pressure depressor for depressing the hypertension in the human body according to claim 1, further comprising:

an adjustable timing circuit, a triggering circuit and a music alarm circuit, wherein said adjustable timing circuit comprising: a third integrated circuit ($IC_3$) of which the pins 11, 10 and 9 are connected respectively with the first terminals of a resistor ($R_5$), a variable resistors ($R_7$) and a capacitor ($C_4$) ;a variable resistor ($R_6$) and a potentiometer W both having first terminals connected with the second terminal of said resistor($R_7$) and a second terminals connected with the seconds terminal of said resistor ($R_5$) and said capacitor ($C_4$); a capacitor $C_5$ being connected between the pin 16 and pin 12; a resistor $R_8$ being connected between the pin 12 and earth ; a switch K being connected between the pin 16 and the positive terminal Vcc of D. C. power supply whose negative terminal is connected to the pin 8 and earth; when the switch K is closed, a control pulse signal (PSD) having a pulse duration of 1~3 second and a period of 10–15 minutes is output from the pin 3, said triggering circuit comprising: a fourth integrated circuit $IC_4$ of which a input pin 1 receives the control pulse signal (PSD) output from the third integrated circuit ($IC_3$) through resistor ($R_9$), and a capacitor ($C_6$) being connected between the pins 3 and 4 of the fourth integrated circuit ($IC_4$ ), and said music alarm circuit comprising: a ceramic buzzer (HTD) having two terminals connected with the capacitor $C_6$ in parallel between the pins 3 and 4 of the fourth integrated circuit ($IC_4$).

6. A blood pressure depressor for depressing the hypertension in the human body according to claim 1, or 2, wherein said hand electrode (M) being a integral electrode with three convex blocks made of zinc and having a 'E' configuration.

* * * * *